United States Patent
Karouzakis et al.

(10) Patent No.: US 6,897,239 B1
(45) Date of Patent: May 24, 2005

(54) USE OF MISOPROSTOL AND/OR METABOLITES OF MISOPROSTOL FOR TREATING SEXUAL DYSFUNCTION IN WOMEN

(75) Inventors: Petros Karouzakis, Athens (GR); Panagiotis Kanakaris, Athens (GR)

(73) Assignee: Lavipharm S.A. (GR)

( * ) Notice: Subject to any disclaimer, the term of this patent is extended or adjusted under 35 U.S.C. 154(b) by 0 days.

(21) Appl. No.: 09/762,602

(22) PCT Filed: Aug. 13, 1999

(86) PCT No.: PCT/GR99/00030

§ 371 (c)(1),
(2), (4) Date: Mar. 21, 2001

(87) PCT Pub. No.: WO00/09134

PCT Pub. Date: Feb. 24, 2000

(30) Foreign Application Priority Data

Aug. 14, 1998 (GR) .......................... 970100172

(51) Int. Cl.[7] ............................................. A61K 31/19
(52) U.S. Cl. ....................................................... 514/573
(58) Field of Search ........................................ 514/573

(56) References Cited

U.S. PATENT DOCUMENTS

| | | | |
|---|---|---|---|
| 5,242,391 A | 9/1993 | Place et al. ............... 604/60 |
| 5,252,602 A | 10/1993 | Alam et al. ............. 514/530 |
| 5,256,652 A | * 10/1993 | El-Rashidy | |
| 5,324,746 A | 6/1994 | McKee et al. .......... 514/530 |
| 5,510,384 A | 4/1996 | McKee et al. .......... 514/530 |
| 5,612,359 A | 3/1997 | Murugesan ............. 514/365 |
| 5,684,177 A | 11/1997 | Lu et al. .................. 560/121 |
| 5,688,499 A | 11/1997 | Banting et al. .......... 424/8.35 |
| 5,708,031 A | 1/1998 | Scott ...................... 514/573 |
| 5,773,457 A | * 6/1998 | Nahoum | |
| 5,877,216 A | 3/1999 | Place et al. ............. 514/573 |
| 5,908,853 A | 6/1999 | Nahoum ................. 514/342 |
| 5,942,545 A | 8/1999 | Samour et al. ......... 514/573 |
| 5,952,361 A | 9/1999 | Nahoum ................. 514/396 |
| 5,962,528 A | 10/1999 | Scott ...................... 514/573 |
| 5,981,563 A | * 11/1999 | Lowrey | |
| 6,046,240 A | 4/2000 | See ........................ 514/573 |
| 6,046,244 A | * 4/2000 | Buyuktimkin et al. | |
| 6,103,765 A | * 8/2000 | Neal | |
| 6,210,343 B1 | 4/2001 | Kanakaris et al. ...... 600/504 |
| 6,277,884 B1 | 8/2001 | Tejada ................... 514/565 |
| 6,299,900 B1 | 10/2001 | Reed et al. ............. 424/449 |
| 6,469,016 B1 | 10/2002 | Place et al. ............. 514/262 |
| 6,593,313 B2 | 7/2003 | Place et al. ............. 514/108 |
| 6,593,369 B2 | 7/2003 | Neal ...................... 514/573 |

FOREIGN PATENT DOCUMENTS

| | | | | |
|---|---|---|---|---|
| EP | 1 108 426 | 6/2001 | ......... A61K/31/00 |
| WO | WO 93/00894 | 1/1993 | ......... A61K/31/195 |
| WO | WO 96/09825 | 4/1996 | ......... A61K/31/557 |
| WO | WO 96/28142 | 9/1996 | ............ A61K/9/00 |
| WO | WO 97/33608 | 9/1997 | ......... A61K/38/22 |
| WO | WO 00/32195 | 6/2000 | ......... A61K/31/475 |
| WO | WO 01/70211 | 9/2001 | ......... A61K/31/00 |
| WO | WO 01/70337 | 9/2001 | ......... A61P/15/00 |
| WO | WO 01/70708 | 9/2001 | ......... C07D/241/02 |

OTHER PUBLICATIONS

Reilly, Chapter 80 "Pharmaceutical Necessities" in Remington: the Science and Pracice of Pharmacy, 1995: p. 1380.*
Cytotec® monograph, Aug., 1995 in Physicians' Desk Reference, 54th ed. 2000, p. 2907–2909.*
Piletz, J. et al., *Plasma MHPG Response to Yohimbine Treatment in Women With Hypoactive Sexual Desire*, Journal of Sex and Marital Therapy, vol. 24, No. 1, p. 43–54, Jan.–Mar. 1998.

(Continued)

Primary Examiner—San-Ming Hui
(74) Attorney, Agent, or Firm—Bromberg & Sunstein LLP

(57) ABSTRACT

Topical application of a prostaglandin directly to the clitoris is effective for enhancing female sexual desire and responsiveness.

25 Claims, 1 Drawing Sheet

STRUCTURAL FORMS
Misoprostol

OTHER PUBLICATIONS

Ernst, E.; Pittler, E.H., *Yohimbine For Erectile Dysfunction*, The Journal of Urology, Feb., 1998; 159 (2):433–436.

Kaplan, S. et al., Abstract: *Safety and Efficacy of Sildenafil in Postmenopausal Women with Sexual Dysfunction*, Urology, vol. 53, issue 3, Mar., 1999, p. 481–488.

*Study: Viagra Ineffective for Female Sexual Dysfunction*, Canada Express RX, http://www.canadaexpressrx.com/viagrasotry29.html., Mar. 8, 1999.

*Sexual Healing Probing the Problem of Sex Dysfunction in Women*, Boston, p. 79, Jun. 2003.

Basson, R. et al., *Efficacy and Safety of Sildenafil Citrate in Women with Sexual Dysfunction Associate with Female Sexual Arousal Disorder*, NCBI, http://www.ncbi.nlm.nih.gov/entrez/query.fcgi?cmd=Retrieve&db=PubMed&listuids=12150, May, 2002.

*Sildenafil for Female Sexual Arousal Disorder*, National Horizon Scanning Centre, Jul. 2002.

Cialis and Levitra News, *Viagra for Women*, http://www.buy-viagra-cialis-levitra.com/news/impotence/00000010.shtml, Mar. 25, 2003.

*Viagra and Women*, http://wowhub.com/ViagraAndWomen.htm.

*Does Viagra Work for Women? Researchers Say Yes!*, http://www.skifriends.com/does-viagra-work-for-women.htm, May 26, 2001.

*Bigger is Better When It Comen to the G Spot*, New Scientist.com, http://www.newscientist.com/news/news/.jsp?id=99992495, Jul. 2, 2003.

Jones, R., *Organ 'G Spot' Documented in Women*, http://www.mercola.com/2002/jul20/orgasm.htm, Jul. 20, 2002.

Finn, R., *Sildenafil: Less SSRI–Related Sexual Dysfunction in Women?*, http://www.natural-hrt.com/artman/publish/article 135.shtml, Mar. 13, 2003.

Goldhill, Jon, *Male and Female Sexual Dysfunction: Blockbuster Indication for Multiple Pharmacological Targets*, http://www.leaddiscovery.co.uk/target-discovery/abstracts/dossier-MDI002.html., Sep. 6, 2002.

Jovanovic, L., *Finally, It Is Our Turn!*, (Abstract), Diabetes Care, 25:787–788, Jan. 31, 2002.

Duncan L. et al., *Sexual Dysfunction in Women. Do Antihypertensive Drugs Have an Impact?*, Drug Safety, Mar., 1993, 8 (3):225–34.

Smith, *Effects of Four Beta–Adrenergic Receptor Antagonists on Male Rat Sexual Behavior*, (Abstract), Pharmacol Biochem Behavior http://www.ncbi.nlm.nih.gov/entrez/query.fcgi?CMD=Display&DB=PubMed, Aug. 1990; 36 (4):713–7.

Mundle, et al. "Vaginal Misoprostol for Induction of Labor: A Randomized Controlled Trial", vol. 88, No. 4 (Part 1), pp. 521–525 (1996).

Carbonell, et al. "Vaginal misoprostol for early second–trimester abortion", The European Journal of Contraception and Reproductive Health Care, vol. 3, pp. 93–98 (1998).

\* cited by examiner

STRUCTURAL FORMS
Fig. 1. Misoprostol
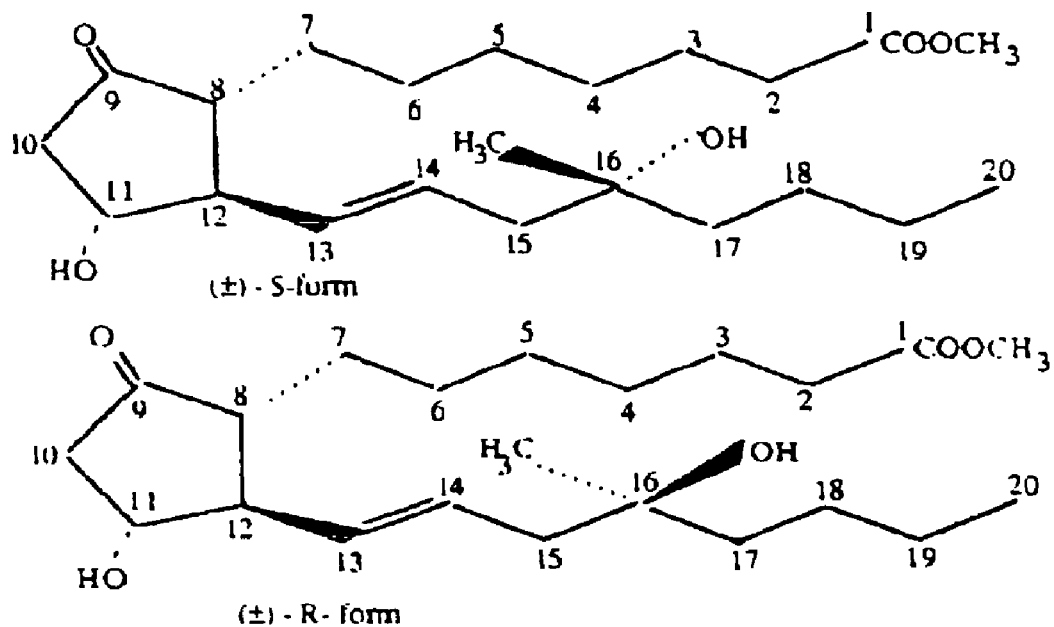
Fig. 2. Misoprostol acid
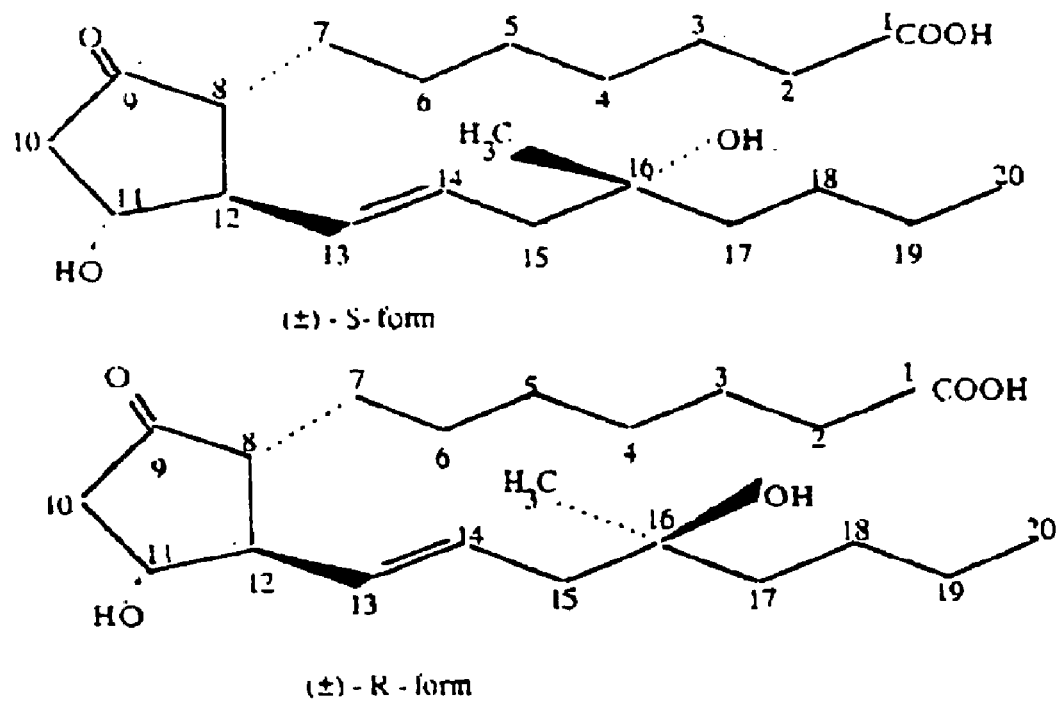

USE OF MISOPROSTOL AND/OR METABOLITES OF MISOPROSTOL FOR TREATING SEXUAL DYSFUNCTION IN WOMEN

The invention relates to the use of an already known pharmaceutical substance, misoprostol as well as its first metabolite, misoprostol acid, for preparation of a drug for external use which is destined to cure sexual dysfunction in women.

The problem of the female sexual dysfunction even though it has been setted by the modern medicine decades ago, it hasn't been yet confronted with efficiency.

The extension of the problem is not quite known (Scrip Reports, March 1998), but according to an older research (Frank et al., 1978) the percentage of women facing a kind of dysfunction is going up to 63%.

In our days the sexual dysfunction of women is being confronted either with surgical restoration, when—rarely—it has to doe with anatomic problems, or with psychotherapy, that could be effective in cases where the causes are not functional, or even with the specific treatment of substitution in cases where sexual inability has to do with hormonal disturbance.

These methods are being confronted with skepticism, or because they are applying to a very small percentage of women (e.g. women with anatomic problems), either because they are characterized by a low efficiency, in accordance—many times—to an adverse relation between benefit and risk.

The interest of many searchers nowdays has been turned to the use of vasoactive substances, in accordance with the methods used in the treatment of male impotence. But these methods even though they are successfully used in men (for example intracavernosal injections), they strike against the female genital system (inability of selfinjection into the corpora cavernosa of the clitoris), either the inefficiency of the methods that are for external use.

The present method aims at the removal of the disadvantages of the above methods with the use of a simple method, that consists of the local application of a vasoactive substance, known as misoprostol, to the clitoris or/and to the vagina, in order to cure sexual dysfunction in women due to vascular, hormonal, phychogenic or other cause.

Misoprostol is the general name of a synthetic prostaglandin belonging to the $E_1$ series ($PGE_1$ analogs). Synthesis: P. W. Collins, R. Pappo, Belgian patent 827,127, U.S. Pat. No. 3,965,143 (The Merck Index, ed. Merck & Co. Inc, $11^{th}$ edition, 1989, p. 6128). Its chemical name is (11a,13E)-(±)-11,16-Dihydroxy-16-methyl-9-oxoprost-13-en-1-oic acid methyl ester or (±)-(methyl)-(1R,2R,3R)-3-hydroxy-2-[(E)-(4RS)-4-hydroxy-4-methyl-1-octenyl]-5-oxocyclopentaneheptanoate or (±)-15-deoxy-(16RS)-16-hydroxy-16-methyl-$PGE_1$ methyl ester. It is consisted of 4 stereoisomers in about equal proportions [(+) & (−) enantiomers of 16R- and 16S-forms]. (The Merck Index, $11^{th}$ edition, 1989, p. 6128). The empirical formula is $C_{22}H_{38}O_5$.

Its structural formula appears in page 8, FIG. 1.

Compared with other prostaglandins of group $E_1$ and especially alprostadil, misoprostol bears a methyl group (—$CH_3$) on the carbon atom of position 16.

According to a method which relates the biological action of various medicament molecules to its chemical structure it appears that due to this group we have a big penetration of misoprostol in the underlying tissues and a local vasodilation which cure sexual dysfunctions. Misoprostol is used today orally as antiulcer drug (Physicians Desc Reference, PDR, ed. Medical Economics Data Production Company at Montrale $48^{th}$ edition, 1994, P. 2197–2199).

In particular it is administered for the prevention of gastric ulcer to patients who take non-steroid antiinflammatory drugs. It is available in the countries of Europe and U.S.A. by Searle Company under the commercial name Cytotec®. In none country is the drug mentioned as suitable for male impotence nor are there any relevant reports on the international bibliography. On a contrary amongst the undesirable effects in oral therapy with misoprostol is male impotence (Physicians Desc Reference, ed. Medical Economics Data Production Company at Montrale, $48^{th}$ edition, 1994, p. 2197–2199).

Misoprostol—compared to other vasodilatory drugs (e.g. nitroglycerin, Prostaglandin $E_1$ etc.)—cause a strong local vasodilation and as a result increase of the blood flow when it is used externally to the clitoris or/and to the vagina. Because of the local vasodilation is caused tumescence of the clitoris, intence bleeding of the vagina and feeling of sexual desire. Simultaneously, in women with anorgasmia of various causes, promote after masturbation or sexual intercourse, the coming of orgasm.

Equally strong topical vasodilation after external application is exerted by the hydrolysis product of misoprostol (misoprostol acid) which anyway constitutes the first misoprostol metabolite after its introduction in the organism (see page 8, FIG. 2).

Last because of the intense topical vasodilatory action of misoprostol and the corresponding free acid, the two pharmaceutical molecules reinforce the absorption of other vasoactive substances (e.g. alprostadil) resulting in the occurrence of synergic action.

Misoprostol can be dissolved in water and its compatibility with excipients provides the opportunity of production of a variety of simple pharmacotechnical forms for external use, which are at the same time very well tolerated by the skin and the mucosa.

From the above mentioned description it appears that the most serious advantage of the method is the manner of administration of the drug (external in combination with the lack of undesirable action in the suggested doses or/and the proposed pharmacotechnical forms) the relatively low cost and especially the most satisfactory result together with corresponding methods.

Amongst the probable methods of application, most advantageous is a synthesis in the gel form of relatively low viscosity which contains 0.3–0.9% w/v misoprostol in the methylform of methylester and/or free acid, a complex forming means as 1.6% w/v a-cyclodextrine and substances suitable for the formation of a gel e.g. hydroxypropyl methylcellulose "3000" 2% w/v, propylene glycol 10% v/v and Water to 100 ml. The gel contains 3–9 mg of active substance per ml.

Method of application: 0.1 (or more, depending on responce) are applied to the clitoris or/and to the vagina.

9 examples related to the pharmacotechnical forms and the ways of application of misoprostol:

1) 0.10 ml gel, relatively low viscosity containing 0.3–0.9% w/v misoprostol for applying to the clitoris or/and to the vagina.

Synthesis:
1-1,Misoprostol 0.3–0.9 g
Hydroxypropyl Methylcellulose "3000" 2 g
Water purified to 100 ml
1-2,Misoprostol 0.3–0.9 g
Sodium Carboxymethylcellulose 2 g Propylene Glycol 25 ml
Water purified to 100 ml
2) 0.10 ml gel of relatively high viscosity, containing 0.30–0.90% w/v in misoprostol for vaginal application.
Synthesis:
2-1,Misoprostol 0.30–0.90 g
Hydroxypropyl Methylcellulose "3000" 4 g
Water purified to 100 ml
2-2,Misoprostol 0.30–0.90 g
Sodium Carboxymethylcellulose 4 g
Propylene Glycol 25 ml
Water purified to 100 ml
3) 0.10 ml of aqueous solution of misoprostol containing 0.3–0.9% w/v for clitoral or/and vaginal application. The solution can also contain propylene glycol or glycerol in the corresponding proportions (e.g. 10%) to increase the viscosity of the solution.
4) 0.10 ml of ointment or emulsion o/w containing 0.3–0.9% w/w in misoprostol for clitoral or/and vaginal application, where misoprostol is found spread in the continuous (aqueous) phase.
Synthesis:
4-1,Misoprostol 0.3–0.9 g
Vanishing Cream to 100 g
(Although for the requirements of this example as Vanishing Cream we used Bepanthene® Cream of Roche, we have various creams o/w which are available in commerce or are described in National Pharmacopoeies and can be used for the same purpose).
5) Vaginal ovules of suitable dimensions, weight about 300–900 mg, containing 0.04–0.20% w/w misoprostol for vaginal use.
Synthesis:
5-1,Misoprostol 0.3–0.9 g
Glycerol 70 g
Gelatine 20 g
Water purified to 100 g
6) 0.10 ml gel (or more depending of response) according to the examples (1-1) and (2-1) which contains moreover 1.6% w/v a-cyclodextrine.
7) 0.10 ml gel (or more depending of response) according to the example (6) which contains moreover 10 ml ethyl alcohol 96° and 0.5 mg/ml alprostadil.
Notes:
1) The incorporation of misoprostol in bases already mentioned took place in normal temperature (20–25° C.) and at a temperature not exceeding 40° C.
2) No significant changes in misoprostol activity was observed as a function of pH, we observent however an important reduction or/and neutralization of misoprostol action in the presence of Polysorbate "80".
3) The time of appearance of the result varies from 20–40 minutes. The timing of the appearance and the intensity of the result seems to be able been positively influenced by certain moisturising agents (e.g. Propylene Glycol, Glycerol) as well as by certain substances which reinforce by various mechanisms the transcutaneous absorption (e.g. Urea, Acid Citric).
4) High once only doses of misoprostol (>1000 mcg to the clitoris or to the vagina) cause certain systematic undesirable effects as shudder, feeling of hard ship, excitement and diarrhea. The presence of a-cyclodextrine reduces the undesirable effects and allows the application once only of higher doses without notable effect on the timing of its action but with positive effect on the intensity result and with prolonging of its duration.
5) The doses which are mentioned in the examples are only indicative since the intensity of the result depends, apart from the nature and the grade of the sexual dysfunction on other factors as e.g. the degree of moisturising of the underlying tissue, the physiological situation of the skin or the mucosa etc. As had already been mentioned, misoprostol is an extremely hydrophile molecule compared with other prostaglandins of $E_1$ series (e.g. with alprostadil which can be dissolved in alcohol but her solubility in water is only 8000 mcg/100 ml at 35° C.).

This consists an important advantage:
a) Because no use of organic factors is required (e.g. ethyl alcohol) which usually irritate tissues and are thus unsuitable for application on the skin and especially the mucus.
b) Because it allows the incorporation of active substances on a very small amount of excipient, suitable for application on surfaces of limited extent, as e.g. the clitoris.
6) Misoprostol hasn't been accused for carcinogenic or teratogenic effect but because of the described irritation of the smooth uterine fibbers (Physicians Desc Reference, PDR, ed. Medical Economics Data Production Company at Montrale 48$^{th}$ edition, 1994, P. 2197–2199), misoprostol must not becoming in touch with the genital system of the women who are pregnant.

What is claimed is:

1. A method for treating sexual dysfunction in a female subject in need of such treatment, comprising:
   (a) providing a vasoactive formulation having an effective dose of a primary vasoactive agent selected from misoprostol and misoprostol acid; and
   (b) topically administering the formulation to the clitoris or vagina of the subject for treating sexual dysfunction.

2. A method according to claim 1, wherein the misoprostol or misoprostol acid is selected from the group consisting of a racemic mixture, an enantiomer in a (+) or (−) R form and an enantiomer in a (+) or (−) S form.

3. A method according to claim 1, wherein the formulation further comprises a second vasoactive agent in addition to misoprostol or misoprostol acid.

4. A method according to claim 3, wherein the second agent is alprostadil.

5. A method according to claim 1, wherein the formulation further comprises: a passage accelerator for increasing absorption of at least one of misoprostol and a metabolite of misoprostol and optionally an additional vasodilator.

6. A method according to claim 1, wherein the formulation further comprises cyclodextrin.

7. A method according to claim 1, wherein treatment of sexual dysfunction further includes enhancement of sexual desire.

8. A method according to claim 1, wherein the formulation further comprises a galenic preparation.

9. A method according to claim 1, wherein the formulation is administered as one of a gel, an aqueous solution, an ointment, vaginal ovules and a system of controlled transdermal absorption.

10. A method according to claim 1, wherein the formulation comprises a gel.

11. A method according to claim 10, wherein the gel contains a polymer having a concentration of less than 4%.

12. A method according to claim 1, wherein the formulation is administered as a vanishing cream.

13. A method according to claim 1, wherein the formulation further comprises gelatin.

14. A method for treating sexual dysfunction in a female subject, comprising:

(a) providing a mixture including misoprostol or misoprostol acid, hydroxypropyl methyl cellulose and water; and (b) topically administering the mixture to a female subject.

15. A method according to claim 10, wherein the effective dose of misoprostol or misoprostol acid is in the range of 0.3–0.9% w/v and the formulation further includes hydroxypropyl methyl cellulose.

16. A pharmaceutical composition comprising:

an effective dose of misoprostol compound and alprostadil in a topical formulation suitable for application to at least one of the clitoris and the vagina, for promoting tumescence of the clitoris in women suffering from sexual dysfunction, wherein penetration of the alprostadil to underlying tissue is facilitated by the misoprostol compound.

17. A pharmaceutical composition according to claim 16 wherein the formulation further comprises a methyl cellulose.

18. A method for treating sexual dysfunction in a female subject in need of such treatment comprising:

providing a vasoactive formulation including a misoprostol or misoprostol acid, but lacking a non-misoprostol penetration enhancer; and topically administering the formulation to the clitoris or vagina of the subject such that penetration to underlying tissue is facilitated by the misoprostol or/and misoprostol acid for promoting tumescence of the clitoris.

19. A method according to claim 18 wherein the formulation further comprises alprostadil.

20. A method according to claim 18 wherein the formulation further comprises cyclodextrin.

21. A method according to claim 18 wherein the formulation further comprises a gel.

22. A method according to claim 18 wherein the formulation further comprises methyl cellulose.

23. A method for treating sexual dysfunction in a female subject comprising:

providing a vasoactive formulation consisting essentially of misoprostol and/or misoprostol acid; and topically administering the formulation to the clitoris or vagina of the subject for treating sexual dysfunction by stimulating vasodilation.

24. A method for treating sexual dysfunction in a female subject comprising:

providing a vasoactive formulation having an effective dose of active agent, the active agent consisting of misoprostol and/or misoprostol acid; and topically administering the formulation to the clitoris or vagina of the subject for treating sexual dysfunction.

25. A method for treating sexual dysfunction in a female subject comprising:

providing a topical formulation having an effective dose of an active agent, the active agent consisting essentially of a mixture of a misoprostol compound and alprostadil; and topically administering the formulation to the clitoris or vagina of the subject for treating sexual dysfunction.

* * * * *